US011786760B2

(12) United States Patent
Graf et al.

(10) Patent No.: US 11,786,760 B2
(45) Date of Patent: Oct. 17, 2023

(54) MULTI-BEAM NEUROMODULATION TECHNIQUES

(71) Applicant: General Electric Company, Schenectady, NY (US)

(72) Inventors: John Frederick Graf, Ballston Lake, NY (US); Christopher Michael Puleo, Niskayuna, NY (US); Jeffrey Michael Ashe, Gloversville, NY (US); Victoria Eugenia Cotero, Troy, NY (US); David Andrew Shoudy, Niskayuna, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 339 days.

(21) Appl. No.: 16/709,717

(22) Filed: Dec. 10, 2019

(65) Prior Publication Data
US 2021/0170203 A1   Jun. 10, 2021

(51) Int. Cl.
*A61N 7/00* (2006.01)

(52) U.S. Cl.
CPC ........ *A61N 7/00* (2013.01); *A61N 2007/0026* (2013.01); *A61N 2007/0052* (2013.01); *A61N 2007/0086* (2013.01)

(58) Field of Classification Search
CPC .............. A61N 7/00; A61N 2007/0026; A61N 2007/0052; A61N 2007/0086; A61N 2007/0073; A61N 2007/0082; A61N 2007/0091; A61N 2007/0095
See application file for complete search history.

(56) References Cited

U.S. PATENT DOCUMENTS

| 7,769,442 | B2 | 8/2010 | Shafer |
| 9,011,336 | B2 | 4/2015 | Slayton et al. |
| 10,070,911 | B2 | 9/2018 | Azamian et al. |
| 10,143,850 | B2 | 12/2018 | Cowan et al. |
| 2008/0033297 | A1 | 2/2008 | Sliwa |
| 2009/0112133 | A1 | 4/2009 | Deisseroth et al. |
| 2010/0030076 | A1 | 2/2010 | Vortman et al. |
| 2010/0081893 | A1 | 4/2010 | Jarvik et al. |
| 2010/0234728 | A1 | 9/2010 | Foley et al. |
| 2011/0172528 | A1 | 7/2011 | Gertner |
| 2012/0197163 | A1 * | 8/2012 | Mishelevich ............ A61N 7/00 601/2 |
| 2012/0296197 | A1 * | 11/2012 | Vahala ..................... A61N 7/02 600/411 |

(Continued)

FOREIGN PATENT DOCUMENTS

WO   WO-2018081826 A1 * 5/2018  ......... A61B 5/04001

OTHER PUBLICATIONS

Mahadevan, Vishy; "Anatomy of the Pancreas and Spleen", Surgery (Oxford), vol. 37, Issue 6, pp. 297-301, Jun. 2019.

(Continued)

*Primary Examiner* — Hien N Nguyen
(74) *Attorney, Agent, or Firm* — Fletcher Yoder P.C.

(57) ABSTRACT

The subject matter of the present disclosure generally relates to techniques for neuromodulation of a tissue that include applying energy (e.g., ultrasound energy) into the tissue at multiple regions of interest, concurrently or consecutively. The neuromodulation may result in tissue displacement, which may be observed through changes in one or more molecules of interest.

19 Claims, 12 Drawing Sheets

(56) References Cited

U.S. PATENT DOCUMENTS

| | | | | |
|---|---|---|---|---|
| 2013/0211293 A1* | 8/2013 | Auboiroux | ............. | H04R 31/00 |
| | | | | 601/3 |
| 2015/0051475 A1* | 2/2015 | Leussler | ................... | A61F 7/00 |
| | | | | 600/411 |
| 2015/0141874 A1 | 5/2015 | Wilson | | |
| 2015/0290476 A1* | 10/2015 | Krocak | ................ | A61B 8/4281 |
| | | | | 601/2 |
| 2018/0207044 A1* | 7/2018 | Sabet | ................... | A61G 13/105 |
| 2019/0076674 A1* | 3/2019 | Ergün | .................... | A61B 18/02 |
| 2020/0302825 A1* | 9/2020 | Sachs | ....................... | G09B 5/02 |

OTHER PUBLICATIONS

PCT/US2020/061327; International Search Report/Written Opinion; dated Mar. 12, 2021; pp. 1-9.
Rahier et al., "Cellular Composition of the Human Diabetic Pancreas", Diabetologia, vol. 24, Issue: 05, pp. 366-371, May 1983.
Martins et al., "Insulin Inhibits LPS-Induced Signaling Pathways in Alveolar Macrophages", Cellular Physiology and Biochemistry, vol. 21, Issue: 4, pp. 297-304, Apr. 23, 2008.
Vikram et al., "Pancreas: Peritoneal Reflections, Ligamentous Connections, and Pathways of Disease Spread", Radiographics : a review publication of the Radiological Society of North America, vol. 29, Issue: 02, Jan. 23, 2009.
Tessaro et al., "Insulin Influences LPS-Induced TNF-A and IL-6 Release through Distinct Pathways in Mouse Macrophages from Different Compartments", Cellular Physiology and Biochemistry, vol. 42, Issue: 05, 2093-2104, Aug. 15, 2017.
Cotero et al., "Noninvasive Sub-Organ Ultrasound Stimulation for Targeted Neuromodulation", Nature Communications, vol. 952, pp. 01-12, Mar. 12, 2019.

* cited by examiner

MULTI-BEAM NEUROMODULATION TECHNIQUES

BACKGROUND

The subject matter disclosed herein relates to neuromodulation and more specifically, to techniques for modulating a physiological response using energy applied from an energy source.

Neuromodulation has been used to treat a variety of clinical conditions. For example, electrical stimulation at various locations along the spinal cord has been used to treat chronic back pain. Such treatment may be performed by an implantable device that periodically generates electrical energy that is applied to a tissue to activate certain nerve fibers, which in turn may result in a decreased sensation of pain. In the case of spinal cord stimulation, the stimulating electrodes are generally positioned in the epidural space, although the pulse generator may be positioned somewhat remotely from the electrodes, e.g., in the abdominal or gluteal region, but connected to the electrodes via conducting wires. In other implementations, deep brain stimulation may be used to stimulate particular areas of the brain to treat movement disorders, and the stimulation locations may be guided by neuroimaging. Such central nervous system stimulation is generally targeted to the local nerve or brain cell function and is mediated by electrodes that deliver electrical pulses and that are positioned at or near the target nerves. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more targeted modulated effect may be more clinically useful.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, an ultrasound system is provided. The ultrasound system includes at least one ultrasound transducer having a plurality of elements. The ultrasound system also includes a controller configured to control a dose of ultrasound energy applied to the subject. The controller is configured to receive image data of tissue of the subject from the ultrasound transducer; divide the image data of the tissue into a plurality of segments representative of the tissue; focus the ultrasound transducer on a plurality of regions of interest, each region of interest being located within a different segment of the plurality of segments; and control the ultrasound transducer to apply ultrasound energy distributed between the plurality of regions of interest to cause tissue displacement of each region of interest.

In one embodiment, a method is provided that includes the steps distributing an ultrasound energy dose between a plurality of regions of interest, wherein each individual region of interest of the plurality of regions of interest receives a fraction of the ultrasound energy dose and wherein a cumulative applied ultrasound energy to the plurality of regions of interest is approximately equal to the ultrasound energy dose; assessing an effectiveness of the ultrasound energy dose; and modifying instructions to apply a subsequent ultrasound energy dose of the neuromodulation treatment based on the assessing.

In one embodiment, a method is provided that includes the steps of receiving image data of a tissue of the subject; dividing the image data of the tissue into a plurality of segments; selecting a plurality of regions of interest in the tissue associated with respective segments of the plurality of segments; and controlling the ultrasound transducer to apply an ultrasound energy dose distributed between the plurality of regions of interest, wherein at least one region of interest of the plurality of regions of interest comprises at least one axon terminal of a neuron, the axon terminal forming a synapse with a non-neuronal cell.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
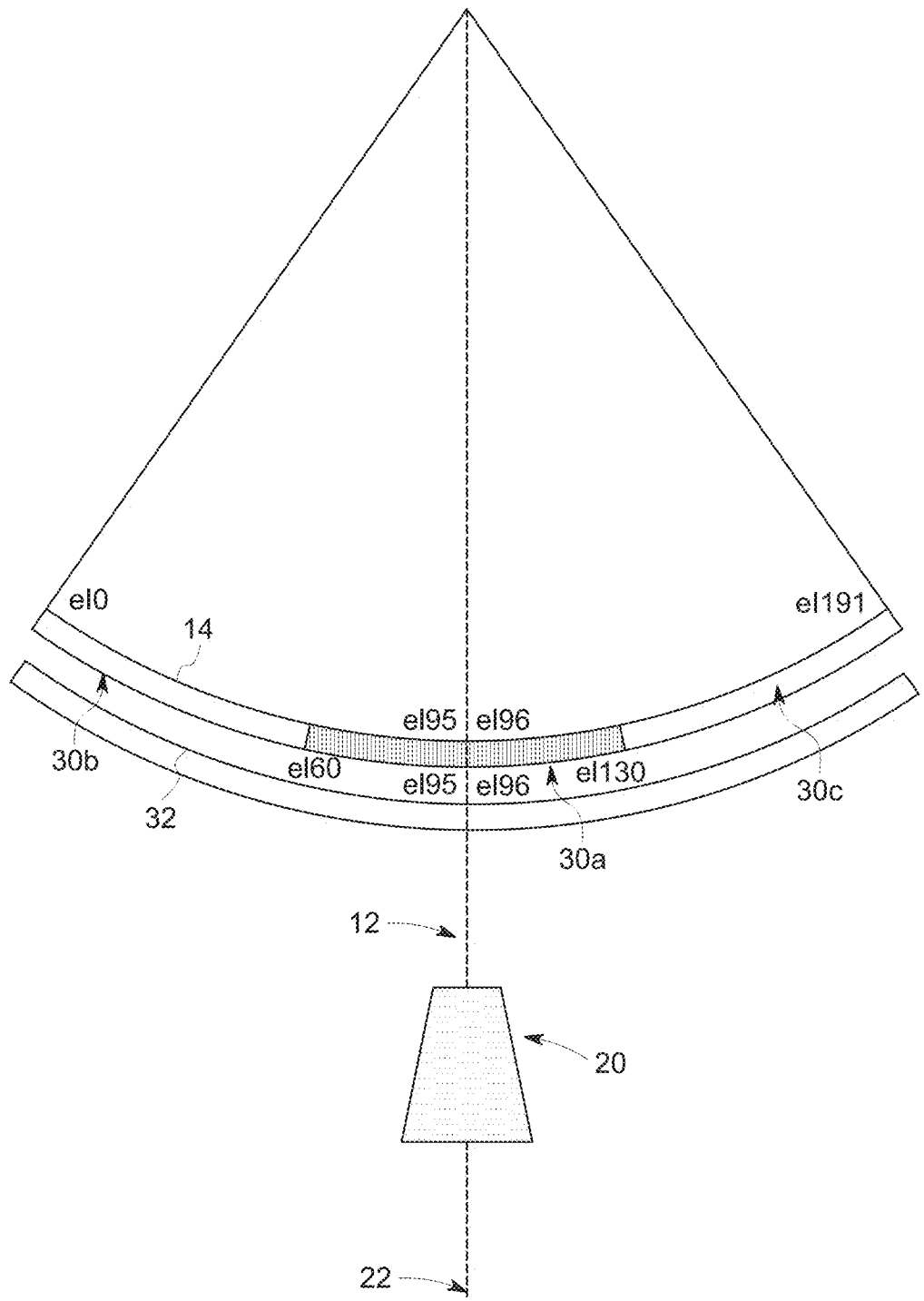
FIG. 1 is a schematic illustration of an ultrasound arrangement including a single ultrasound beam.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments," "in some embodiments," and "in one (an) embodiment."

As provided herein, non-invasive ultrasound stimulation devices may be used to vibrate targeted tissues within the body at multiple locations (i.e. multiple anatomical stimulation locations with different physiological functions) and cost-effectively modulate multiple pathways and/or modulate specific therapeutic effects. Furthermore, dual and multi-beam ultrasound devices may deliver a concurrent stimulation dose to multiple tissues. Most physiological functions are controlled and modulated by multiple molecules under neural and humoral pathway and network controls. Provided herein are techniques that facilitate therapeutic treatments by causing displacement in the body at multiple stimulation sites. This is achieved by the application of a non-invasive ultrasound stimulation device targeting and displacing tissues at multiple locations within the body. It may also be accomplished using ultrasound devices that may deliver stimulation doses to multi-tissues either concurrently or consecutively. The stimulation of multiple anatomical tissue locations may modulate different physiological functions and/or modulate a specific therapeutic effect. Furthermore, the techniques facilitate treatments that may be tailored to provide complementary therapeutic interventions.

Traditional pharmaceuticals are designed to bind to or effect specific molecular targets. Therefore performing multi-pharmacological target or multi-system treatments using traditional pharmaceuticals may involve administering multiple drugs, which is costly, may involve complicated administering protocols, and may expose the subject to multiple side-effects. For example, each drug in a multi-drug treatment will have its own ADME (absorption, distribution, metabolism and excretion) profile. These differences in the ADME profile and the overall differences in each drug's pharmacokinetics and clearance rates will impact the side-effects of each individual drug. The neuromodulation techniques disclosed herein may avoid the side effects of pharmaceutical treatments and provide more individualized therapy options.

Stretch and/or displacement may be induced into tissues in multiple ways (naturally occurring physical motions, mechanical actuators, ultrasound, electromagnetic, optical, implantable devices). Ultrasound is unique in its properties to control focus and shape while simultaneously penetrating deeply into tissue and may be quickly and efficiently applied to multiple stimulation sites. Accordingly, non-invasive ultrasound neuromodulation systems and methods as disclosed herein may be used to vibrate (displace) targeted tissues at multiple locations within the body (i.e. multiple anatomical stimulation locations with different physiological functions). The neuromodulation techniques may be used in conjunction with a neuromodulation system configured to be used to deliver neuromodulating energy as part of a treatment protocol to cause tissue displacement.

FIG. 1 is an example of an ultrasound arrangement that may be used in conjunction with the disclosed techniques in which an ultrasound beam may be steered to consecutively focus on different regions of interest in the tissue of a subject. A single ultrasound beam 12 is shown being emitted by an ultrasound transducer 14 that includes multiple elements that may be individually addressed (activated) to focus on an operator-selected region of interest 20 in a subject's tissue. The region of interest 20 is generally along the axis of the beam 12, and may be controlled to be deeper (e.g., towards tissue depth 22) or shallower (closer to the transducer 14) depending on the beam focus. The axis of the ultrasound beam 12 is dependent on the active sub-aperture 30a, which includes 71 elements of the 192 elements of the transducer 14 by way of example, and by the relative timing of the signals applied to each element. While the beam axis is most efficient when aligned to the sub-aperture, steering the focal region by using timing delays gives more flexibility without much loss of efficiency. However, activation of adjacent elements 30b, 30c or a different subset of elements will cause a different beam axis of the emitted ultrasound beam 12, and a different location of the region of interest 20. Accordingly, as provided herein, the arrangement of FIG. 1 may be used to target multiple consecutive regions of interest 20 in a single organ or tissue structure or distributed between two or more organs or tissue structures. In one embodiment, a single ultrasound dose may be distributed between two, three, four, five, or more regions of interest 20.

Figure 2:
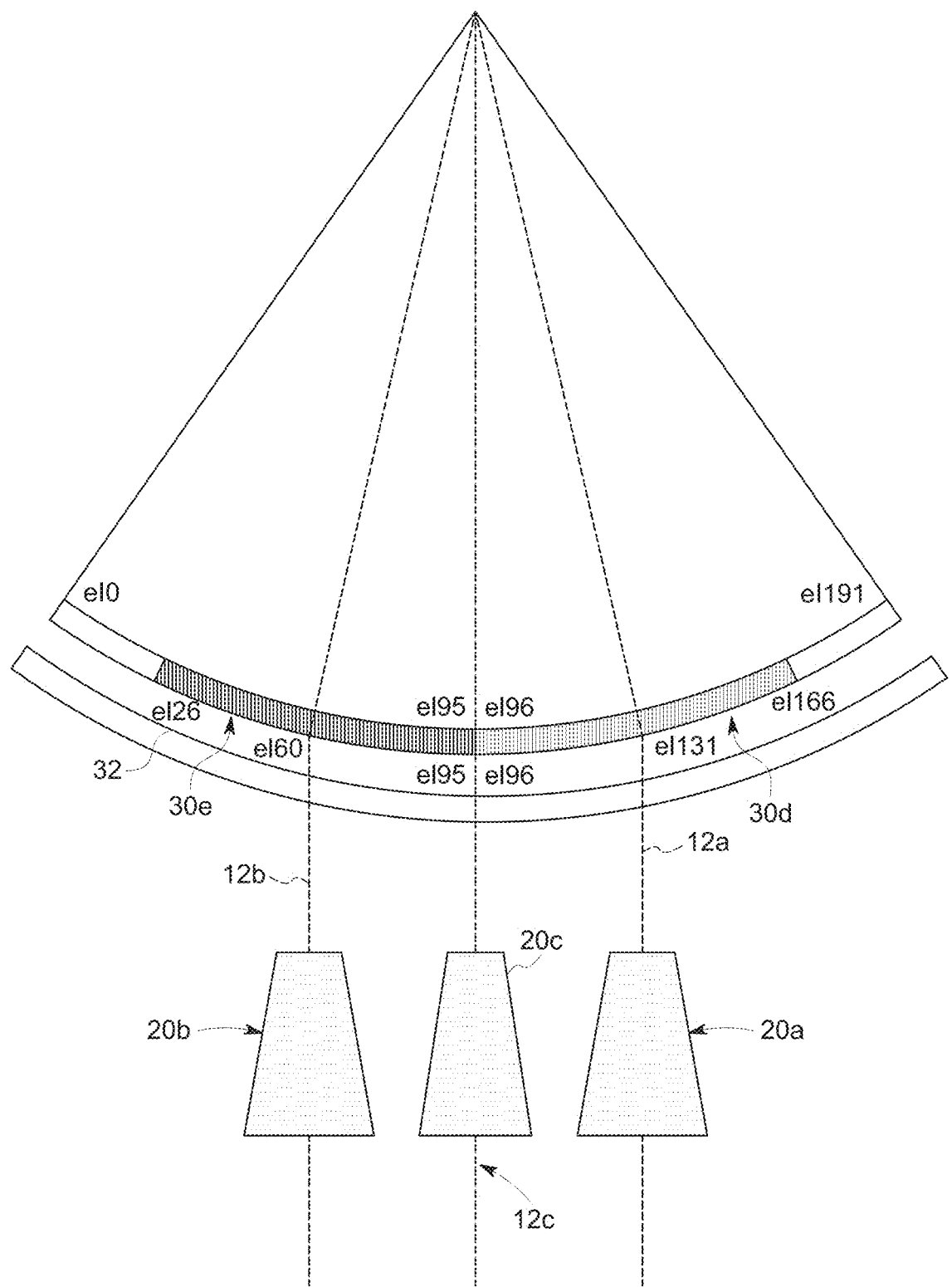
FIG. 2 is a schematic illustration of an ultrasound arrangement including concurrent ultrasound beams.

FIG. 2 shows a schematic illustration of an alternate arrangement in which the transducer 14 is controlled to emit multiple ultrasound beams 12a, 12b concurrently via respective sub-apertures 30d, 30e to target multiple anatomical tissue sites concurrently, e.g., regions of interest 20a, 20b. Accordingly, as provided herein, the arrangement of FIG. 2 may be used to target multiple concurrent regions of interest 20 in a single organ or tissue structure or distributed between two or more organs or tissue structures. In one embodiment, a single ultrasound dose may be distributed between two, three, four, five, or more regions of interest 20.

It should be understood that the depicted examples in FIGS. 1-2 may be combined with one another, and the transducer 14 may also emit a consecutive ultrasound beam 12c in a different direction to target one or more additional regions of interest 20c. Further, in an embodiment, an operator may provide a user input defining a single region of interest (e.g., region of interest 20c), and the disclosed techniques may automatically distribute the ultrasound dose between two, three, or more different regions of interest (e.g., regions of interest 20a, 20b) that are spaced apart from the user-defined region of interest 20c and according to rules-based logic as generally disclosed herein. The ultrasound transducer 14, when in position at a treatment site 32 on the subject' skin, as shown in FIGS. 1-2, is capable of being steered without moving the ultrasound transducer 14 relative to the treatment site 32. The ultrasound transducer 14 may be controlled to treat a range of potential sites, consecutively or concurrently, within the focal range of the transducer 14, which depends on the length, number of elements, and radius of curvature of the selected transducer 14.

The disclosed multi-beam stimulation techniques may be used in conjunction with multiple stimulation sites (region of interest) in a single organ or tissue structure target, such as a liver, pancreas, gastrointestinal tissue, or immune structure such as a spleen or lymph node. The disclosed multi-beam stimulation techniques may be used in conjunction with one or more stimulation sites (region of interest) distributed between two or more organ or tissue structure targets as disclosed herein. While certain examples are disclosed in the context of particular organs or regions of interest, such as the spleen and/or pancreas, it should be understood that other targets are also contemplated within the scope of the disclosure. Accordingly, the disclosed multi-beam stimulation techniques may be used to apply an ultrasound energy dose to two or more regions of interest in a liver, pancreas, gastrointestinal tissue, spleen, and/or lymph node.

A human multi-site ultrasound targeting study was performed to assess inflammatory state modulation as a result of ultrasound neuromodulation. As disclosed herein, ultrasound was used to cause tissue displacement vibrations of a target tissue and, in some cases, the neighboring tail of the pancreas by way of example. The ultrasound dose of tissue displacement was modulated in the study, with different dose levels being applied to different study groups. Modulation of white blood cells to inhibit the release of pro-inflammatory marker TNF-alpha was observed in response to different concentrations of lipopolysaccharide (LPS) exposure. The blood TNF-alpha response to LPS assay was used to characterize a subject's inflammatory state. Targeting the spleen and the Cholinergic Anti-inflammatory Pathway (CAP) system of the spleen may result in the observed dampening of TNF-alpha release by immune cells. Targeting the tail of pancreas and the beta cells of the pancreas to release insulin may also modulate the inflammatory state, i.e., further inhibiting TNF-alpha release by white blood cells). Observed changes in blood glucose measures relative to pre-stimulation baseline were used as a surrogate for insulin release from pancreas. The change in 1 hour post blood glucose change vs. baseline (pre stimulation) time point characterized the effective insulin release and insulin sensitivity of the subject.

Groups of human subjects received a sham control ultrasound dose, a half power dose of 200 mW/cm$^2$ spatial peak temporal average intensity (Ispta), or a full power dose of 400 mW/cm$^2$ (Ispta). The ultrasound dose for the subjects receiving ultrasound energy was distributed between multiple regions of interest (e.g., stimulation sites). The experimental group was stimulated in one or more spleen regions of interest. Certain subjects were also stimulated in a tail of the pancreas. The spleen sites were selected to examine the effects of ultrasound stimulation at different locations within the spleen. For example, the hilum of the spleen is a landmark for locating the spleen using ultrasound imaging and may be used to identify the orientation and locations of other sites in the spleen. The tail of the pancreas is located next to the hilum of the spleen. The study examined the effects of ultrasound stimulation using one or more regions of interest aligned with the hilum of the spleen.

FIGS. 3-6 show ultrasound images with annotated marking showing organ locations and regions of interest for different subjects in a human ultrasound study. The regions of interest are in the spleen and, in certain subjects, a pancreas region. The subjects were stimulated with ultrasound according to different dose parameters and at treatment sites as generally shown in the annotated images. The subjects were subject to fasted blood draws to assess various blood molecule concentrations at baseline and at different time points (1 hour, 2 hours, 24 hours) subsequent to the ultrasound stimulation. FIGS. 3-6 are subjects from study groups in which the total administered dose was a half-power dose of 200 mW/cm$^2$ (temporal average intensity), split between multiple sites, either two or three sites, and at different locations in the spleen and/or pancreas.

Figure 3:
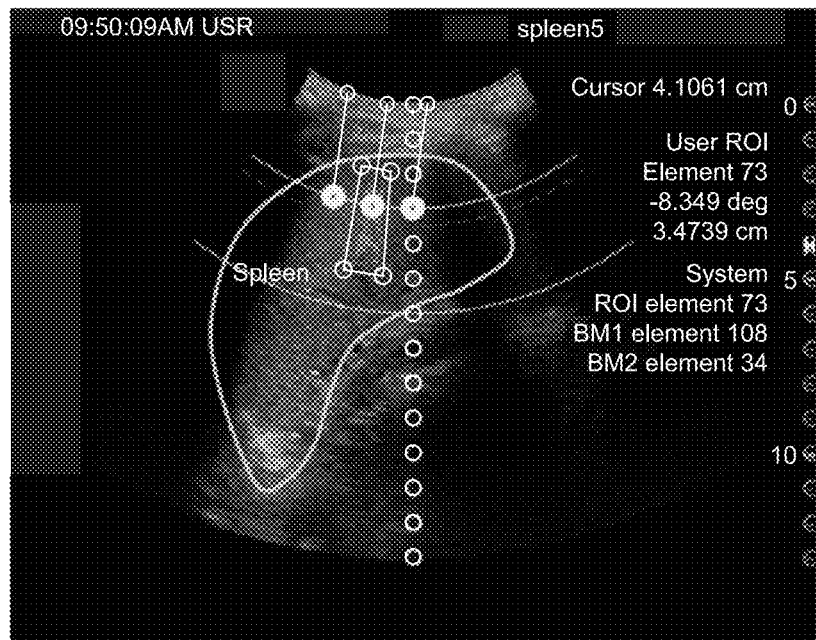
FIG. 3 is an annotated ultrasound image of a subject treated with an ultrasound stimulation showing regions of interest to which ultrasound energy was directed.
Figure 4:
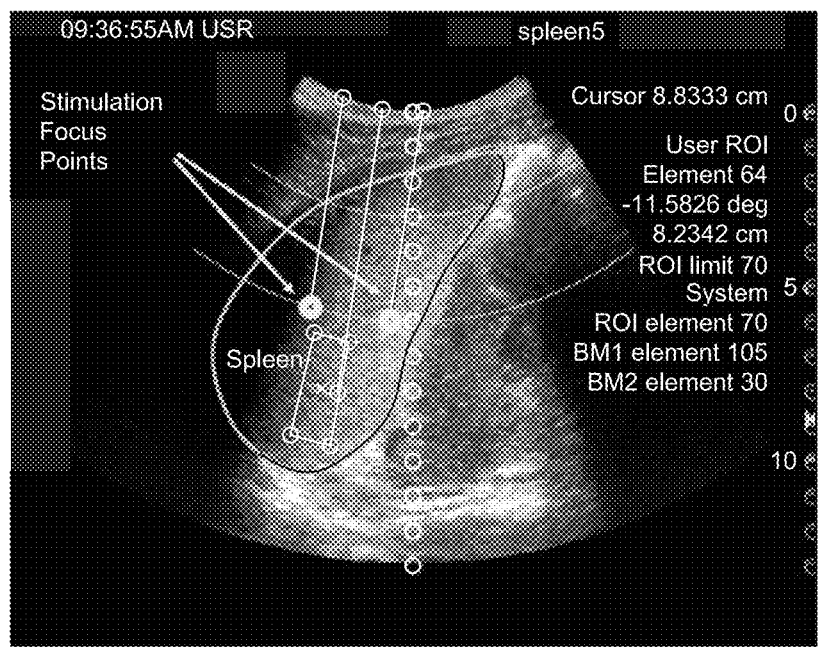
FIG. 4 is an annotated ultrasound image of a subject treated with an ultrasound stimulation regions of interest to which ultrasound energy was directed.
Figure 5:
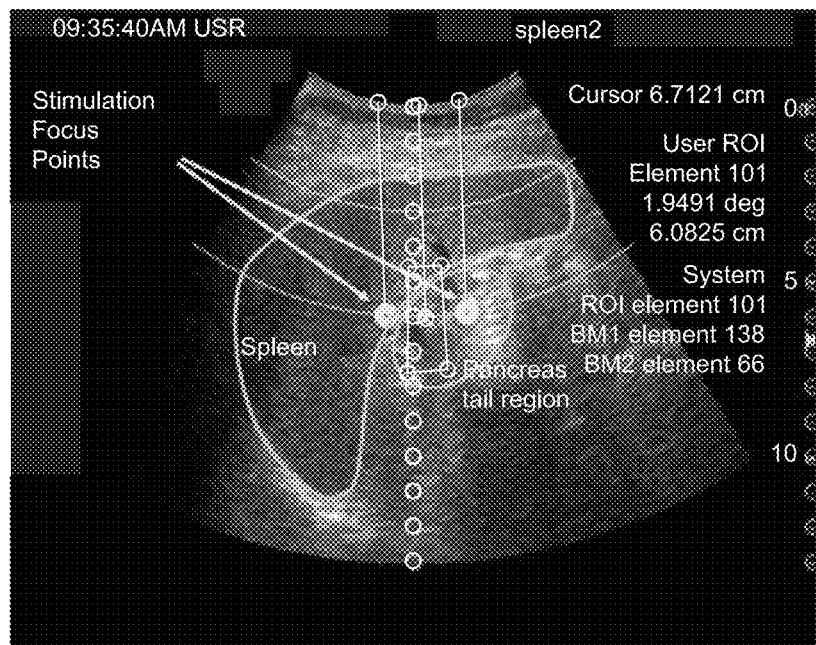
FIG. 5 is an annotated ultrasound image of a subject treated with an ultrasound stimulation regions of interest to which ultrasound energy was directed.
Figure 6:
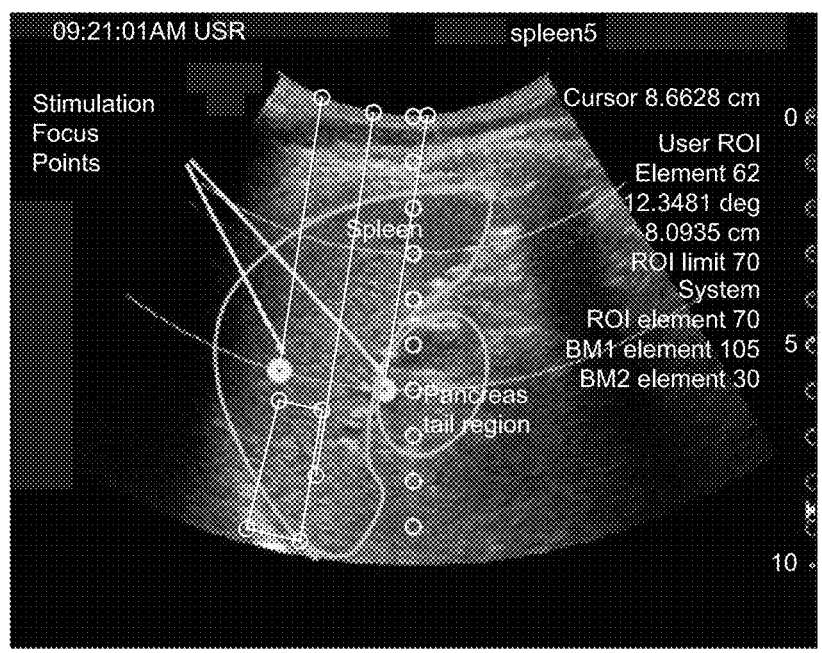
FIG. 6 is an annotated ultrasound image of a subject treated with an ultrasound stimulation regions of interest to which ultrasound energy was directed.

FIG. 3 shows an ultrasound image of a subject who received a half-power dose distributed between three different locations in the spleen. The subject's blood glucose increased 11.7% relative to pre-stimulation baseline at 1 hour post-treatment. FIG. 4 shows an ultrasound image of stimulation using two beams all in the spleen. The subject's blood glucose decreased 6% relative to pre-stimulation baseline at 1 hour post-treatment. FIG. 5 shows an ultrasound image of stimulation using two beams one in the spleen and one in the tail of the pancreas. The subject's blood glucose decreased 31% relative to pre-stimulation baseline at 1 hour post-treatment. FIG. 6 shows an ultrasound image of stimulation using two beams one in the spleen and one in the tail of the pancreas. The subject's blood glucose decreased 38% relative to pre-stimulation baseline at 1 hour post-treatment. The subjects in FIG. 3-6 are generally consistent with the study results in which treatment at two different organ sites resulted in overlapping physiological effects and a greater observed decrease in a concentration of a molecule of interest relative to baseline as a result of ultrasound stimulation.

Figure 7:
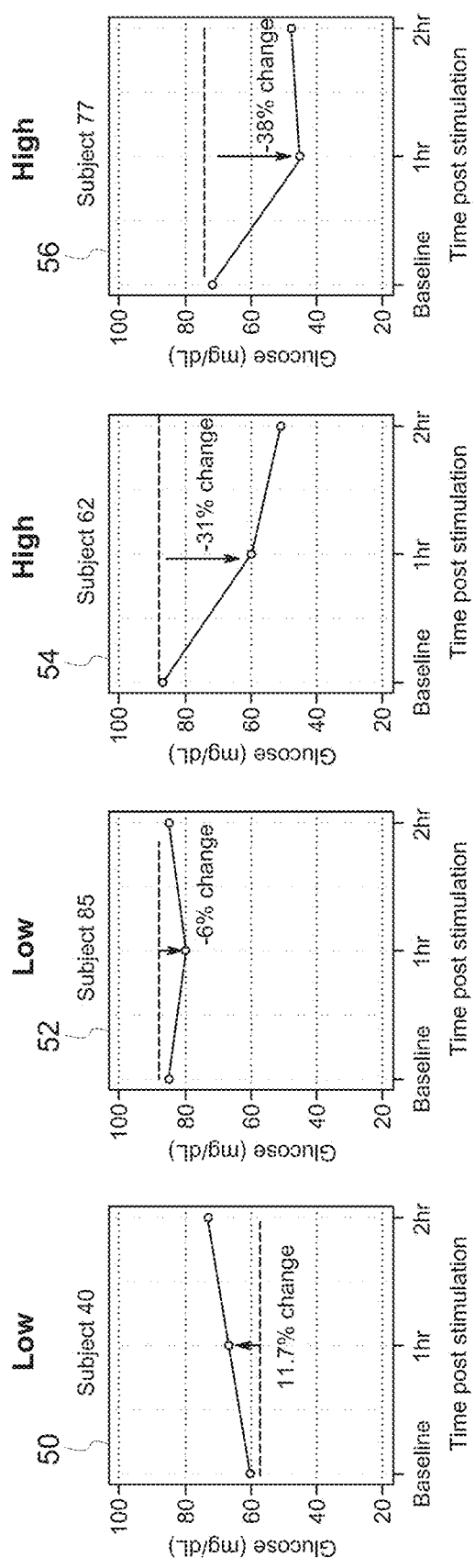
FIG. 7 shows plots of fasted blood glucose levels at various time points for the subjects of FIGS. 3-6.

FIG. 7 shows fasted blood glucose concentrations for the subjects of FIGS. 3-6 at 1 and 2 hours post-stimulation relative to pre-stimulation baseline. Subjects in the study were categorized into low and high pancreas stimulation glucose response groups. The threshold value of 12% for the fasted blood glucose change at 1 hour was used to classify the subjects as low or high. This threshold value was defined using the median value of the absolute % blood glucose change at 1 hour post stimulation for the total of 39 subjects in the study. Therefore, 50% of the subjects in the study were low and the other 50% were classified as high. Plot 50 (see FIG. 3) and plot 52 (see FIG. 4) are plots of subjects categorized as being in the low glucose response group, and plot 54 (FIG. 5) and plot 56 (FIG. 6) are plots of subjects categorized as being in the high glucose response group. Accordingly, pancreas and spleen combined stimulation were indicative of categorization in the high response group.

Figure 8:
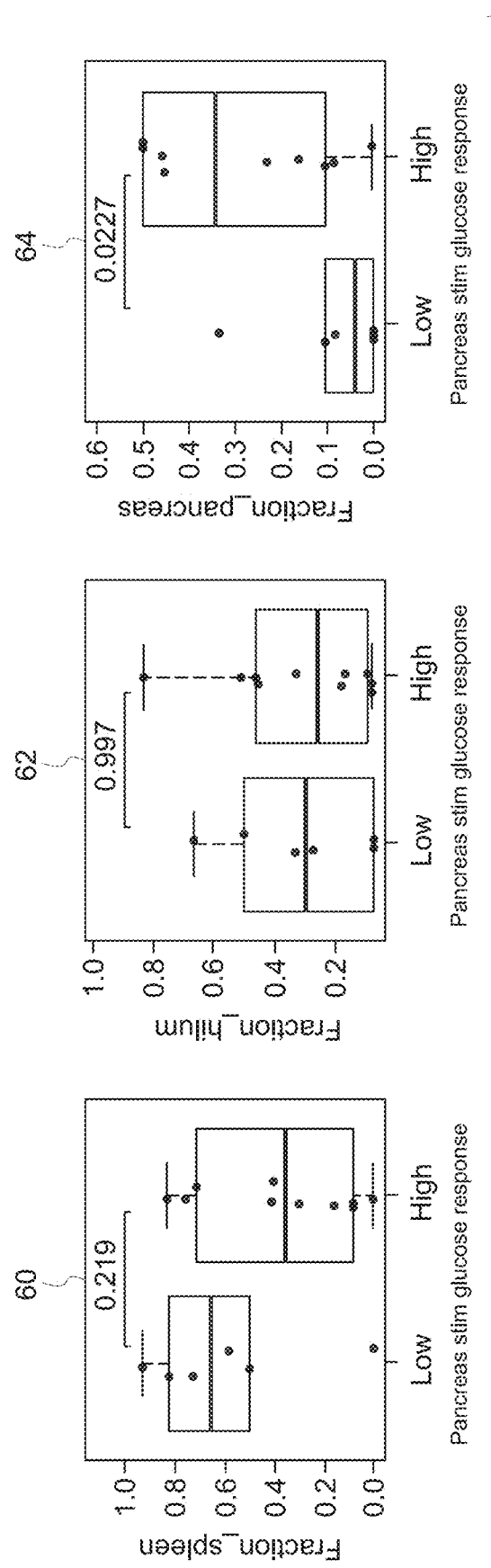
FIG. 8 shows plots of a fraction of ultrasound dose in the spleen, hilum, and pancreas for subjects at half power stimulation doses.
Figure 9:
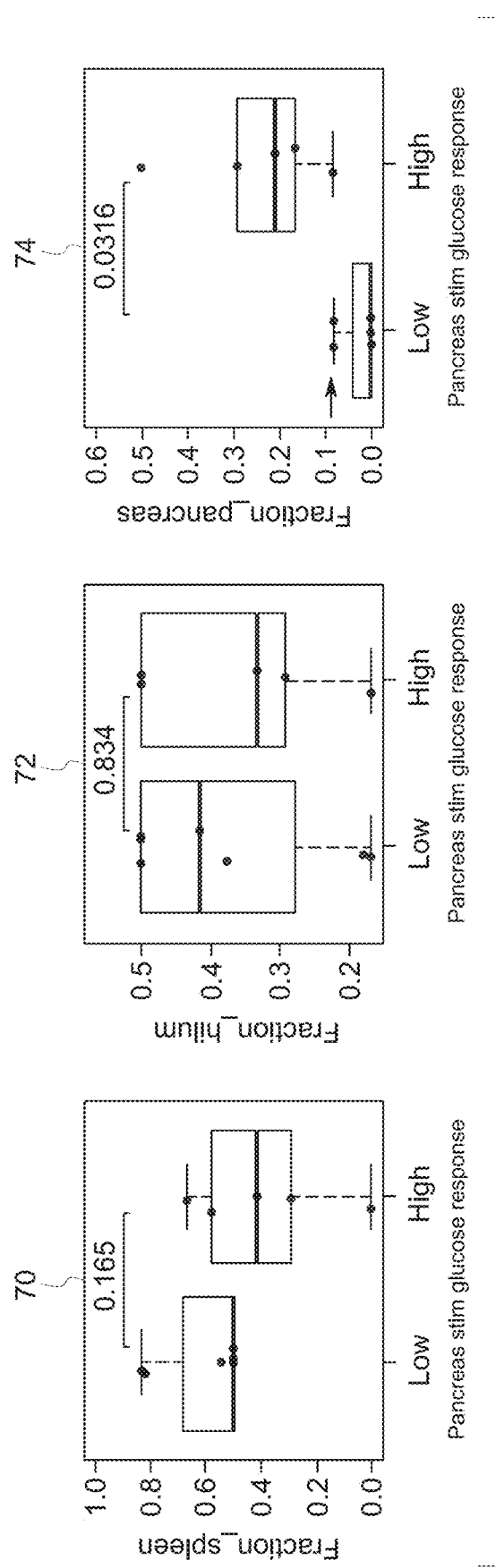
FIG. 9 shows plots of fraction of ultrasound dose in the spleen, hilum, and pancreas for subjects at full power stimulation doses.

FIG. 8 shows plots for the fraction of the ultrasound dose in the spleen (plot 60), hilum (plot 62), and pancreas (plot 64) for the 16 subjects in the half power group. FIG. 9 shows plots for the fraction of the ultrasound dose in the spleen (plot 70), hilum (plot 72), and pancreas (plot 74) for the 12 subjects in the full power group. The subjects were categorized into two groups: low and high pancreas stimulation glucose response groups based on a reduction in blood glucose at 1 hour post stimulation vs baseline pre-stimulation. More than an absolute 12% change were classified as high, and otherwise the subjects were considered low glucose responders. Subjects with greater fraction of the ultrasound dose in the pancreas had a greater reduction in glucose one hour post stimulation (plots 64, 74). A full power stimulation dose fraction of approximately 10% to the pancreas may be enough to cause a reduction in glucose (indicated by arrow in plot 74). Blood glucose change at 1 hour post stimulation was used as a surrogate measure of insulin release from the tail of the pancreas. This surrogate measure also was indicative of the individual subject's insulin sensitivity. The highest concentration of insulin producing beta cells and extractable insulin is in the tail of the pancreas. Stimulation of the tail of the pancreas with ultrasound triggered a release of insulin into the blood stream, causing a significant drop in blood glucose at 1 hour post stimulation in the high responder group.

Figure 10:
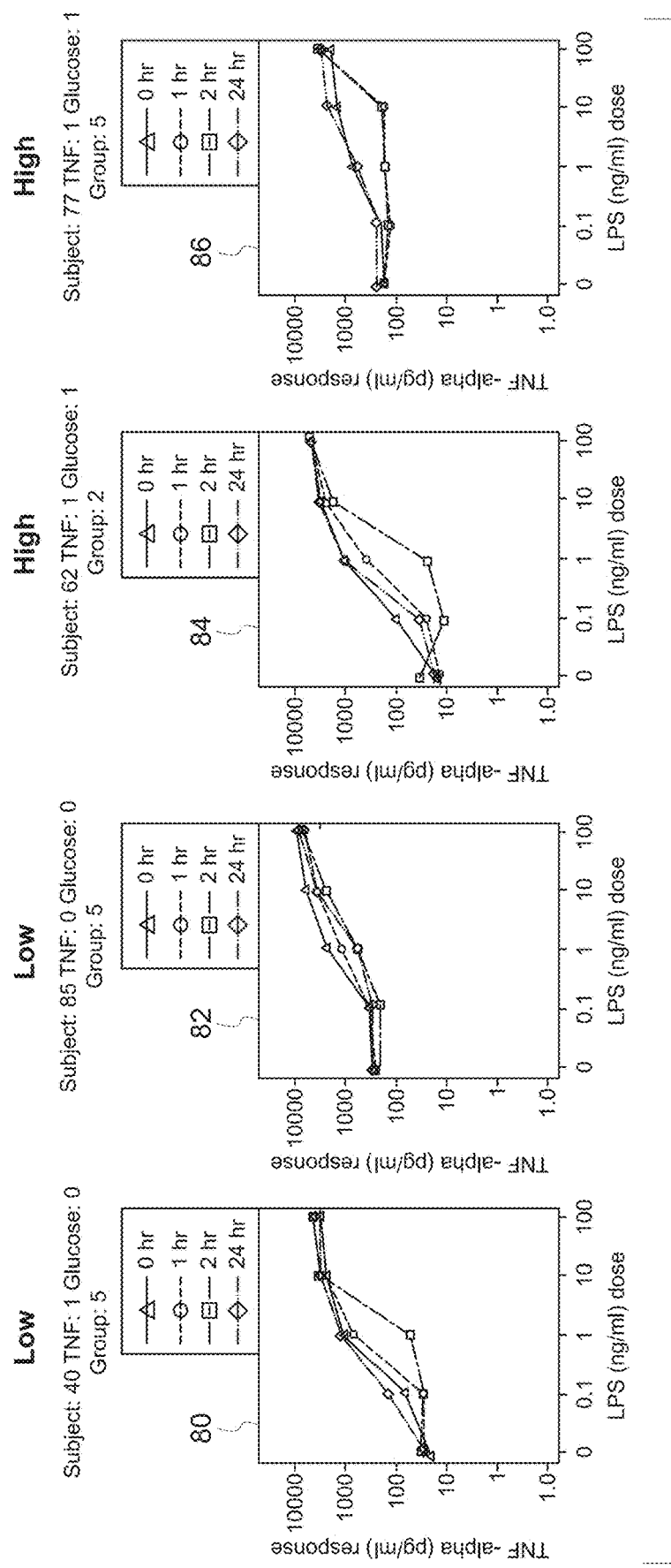
FIG. 10 shows plots of blood TNF-alpha levels at various time points for the subjects of FIGS. 3-6.
Figure 11:
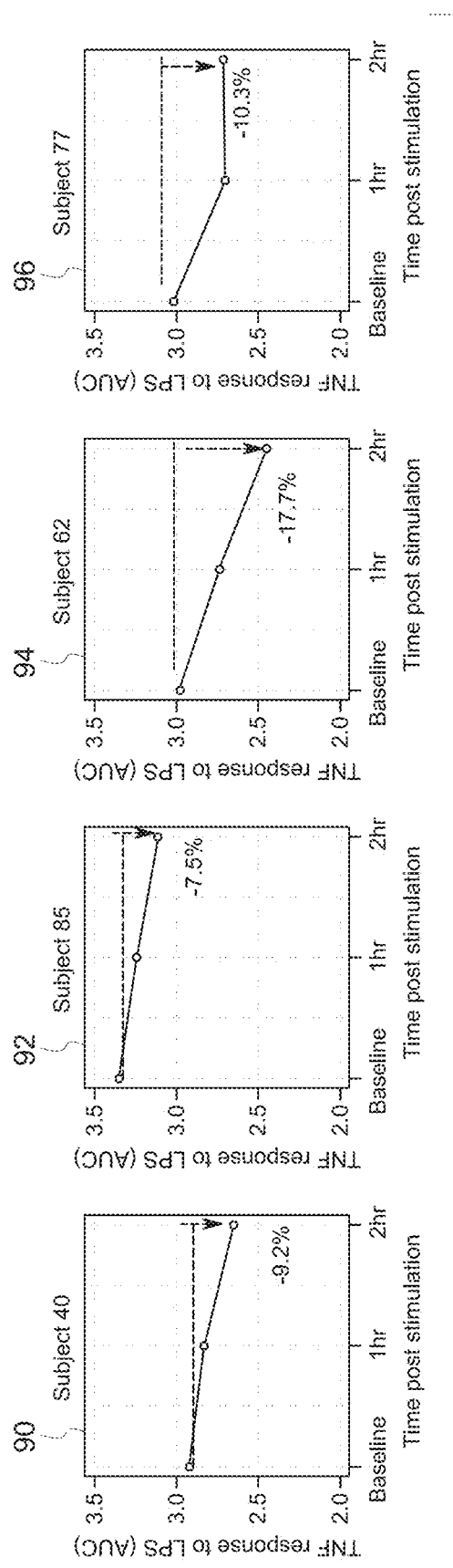
FIG. 11 shows plots indicating changes in blood TNF-alpha levels at various time points and relative to baseline for the subjects of FIGS. 3-6.

Ultrasound stimulation of the spleen may also inhibit the release of TNF-alpha from macrophages and white blood cells. FIG. 10 shows results of TNF-alpha release in the blood at various time points for individual subject of the study and in response to LPS administration at baseline. Plot 80 (see FIG. 3) and plot 82 (see FIG. 4) are plots of subjects categorized as being in the low glucose response group, and plot 84 (FIG. 5) and plot 86 (FIG. 6) are plots of subjects categorized as being in the high glucose response group. FIG. 11 shows TNF-alpha change relative to baseline at 1 hour and 2 hour post stimulation for the subjects of FIG. 10, with the low glucose responders (plot 90 and plot 92) being associated with lower overall decrease or dampening of TNF-alpha release relative to the high glucose responders (plot 94 and plot 96). The results demonstrate a potential insulin-mediated modulation and reduction of TNF-alpha release by immune cells.

Figure 12:
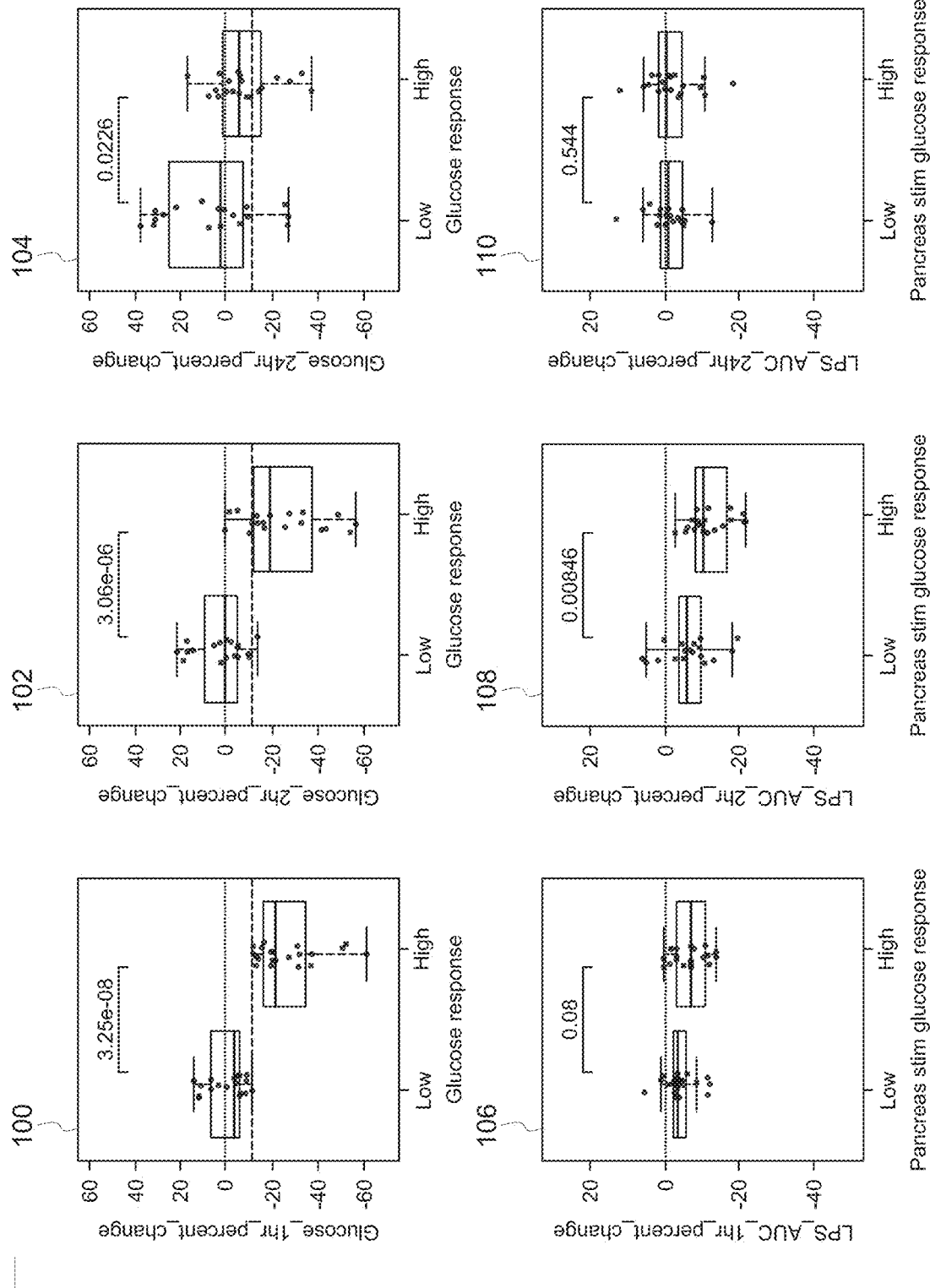
FIG. 12 shows plots of fasted blood glucose and TNF-alpha levels for subjects in the study.

FIG. 12 shows fasted blood glucose changes (plots 100, 102 104) and change in area under the curve for TNF-alpha response (plots 106, 108, 100) at 1, 2, and 24 hours relative to pre-stim baseline for low and high glucose responder groups for 39 human subjects. Those subjects in which the pancreas was stimulated with the spleen had a higher insulin release, greater glucose reduction, and a greater reduction in the observed TNF-alpha response to LPS. The results demonstrate that targeting CAP in the spleen and insulin release from the pancreas modulated the inflammatory state of the subject.

Figure 13:
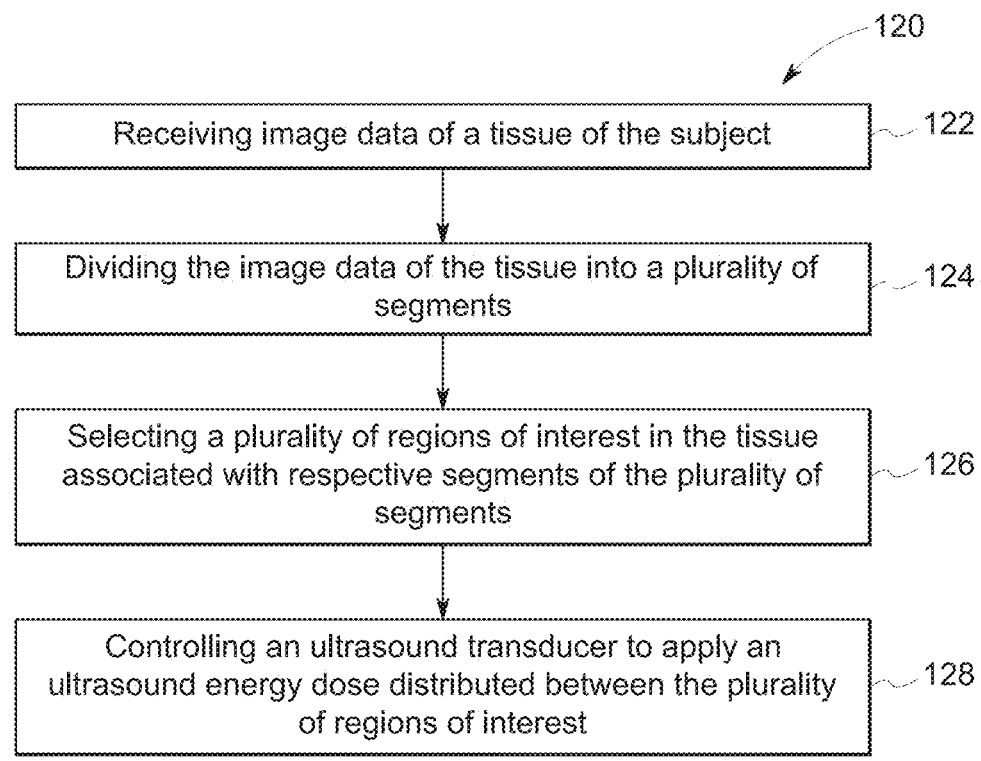
FIG. 13 is a schematic illustration of segmented tissue according to embodiments of the disclosure.

FIG. 13 is a flow diagram of a method 120 for multi-site neuromodulation via ultrasound energy application to a target tissue. In the method 120, the target tissue is imaged to generate image data (block 122), which is accessed or received by the ultrasound system. The image data may be generated by the ultrasound transducer 14 operating in an imaging mode. In another embodiment, a dedicated imaging transducer may be used at the treatment site 32 to generate the image data. Once received, the target tissue is divided into a plurality of segments (block 124). A plurality of regions of interest are selected, whereby each region of interest is associated with a different segment of the segments (block 126). The ultrasound transducer 14 is controlled to apply an ultrasound energy dose distributed between the selected regions of interest (block 126). The ultrasound energy application causes desired effects in the region of interest, such as tissue displacement, which may be assessed via proxy measurements of neuromodulation effectiveness, as generally provided herein.

Figure 14:
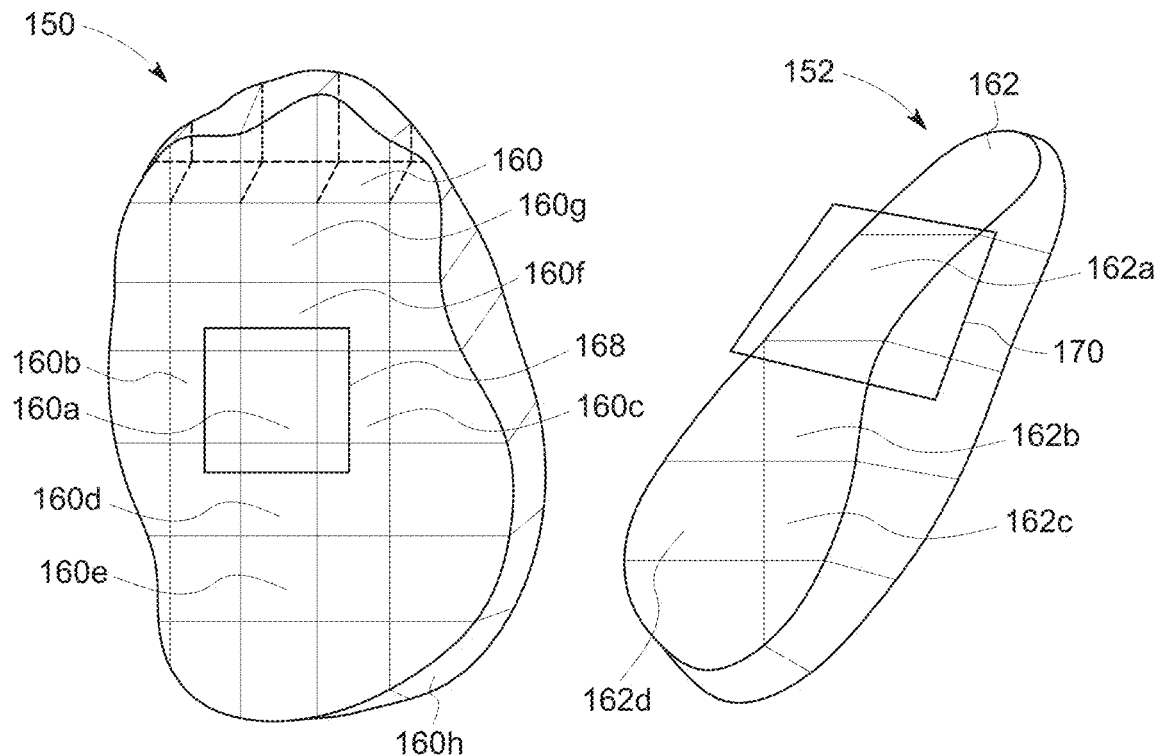
FIG. 14 is a flow diagram of a method of applying a distributed ultrasound dose according to embodiments of the disclosure.

FIG. 14 is a schematic diagram of a first organ 150 and a second organ 152 that may be least partially imaged and present in the image data (FIG. 13) by way of example. However, it should be understood that the disclosed techniques may be applied to a single organ or a two or more organs or non-organ tissue structures. Further, the image data may include only partial images of an organ of interest. The identification of the first organ 150 or the second organ 152, including organ borders and general shape within the image, may be via organ segmentation algorithms, user input, or via a neural network as generally disclosed in U.S. patent application Ser. No. 16/567,996, filed on Sep. 11, 2019, and generally incorporated by reference in its entirety for all purposes.

The identified first organ 150 and second organ 152 may be divided into a plurality of segments. For example, the first organ may be divided into a plurality of first organ segments 160 and the second organ may be divided into a plurality of second organ segments 162. The rules governing a number of segments 160, 162 may be preset by the user or the system. In an embodiment, a user may generally identify an area 168, 170 roughly corresponding to a region of interest via a user interface, for example by drawing or otherwise selecting a portion of a desired size. Once selected, the system may then divide the first organ 150, 152 into the plurality of segments 160,162 that approximately correspond in size to the selected area 168, 170. In another embodiment, the system may have predetermined rules based on the identified organ type, a focal limit of the transducer 14, and the desired ultrasound energy dose for dividing the organ into the plurality of segments 160,162. The segments 160, 162 may or may not be of approximately equal volume.

The segments may rendered visible, with segment borders being indicated on an image generated by the image data. In an embodiment, the user may select a desired segment/s as a region of interest 20 by clicking or otherwise interacting with the visible segments on a display. Alternatively, in cases where the segment borders are visible or not visible on the image, the user may indicate the area 168, 170 corresponding to one or more regions of interest 20, and the system may correlate the selected area 168, 170 to the corresponding segment/s 152, 162. For example, a user may generally indicate the first area 168 corresponding to a particular segment 160*a* on the first organ 150 and the second area 170 corresponding to a particular segment 162*a* in the second organ 152. Once selected, the system may use these segments 160*a*, 162*a* as the regions of interest and may steer the ultrasound transducer 14 to apply ultrasound energy to or within the tissue to locations corresponding with the segments 160*a*, 162*a*.

In an embodiment, the disclosed techniques may automatically select the region/s of interest 20 based on user input. For example, the user may indicate a desired distribution of the ultrasound energy to three sites, two in the first organ 150 and one in the second organ 152. The user may select a first region of interest 20 associated with the segment 160*a* and a second region of interest 20 associated with the segment 162*a*. The system may then select the third region of interest 20 in the first organ 150 using rules-based logic to, for example, avoid adjacent segments (e.g., 160*b*, 160*c*, 160*d*, 160*f*) and to select a spaced-apart segment 160*e*, 160*g*. In another example, the user may select a first region of interest 20 associated with the segment 160*a*, and the system may, based on the input, distribute the dose around the selected region of interest 20, e.g., using two adjacent segments (e.g., 160*b*, 160*c*, 160*d*, 160*f*). In another example, the system may have stored protocols in which the segments are ranked based on empirical effectiveness information, and the selection may be based on the ranking. In one example, the segment 162 may be a top ranked segment, while adjacent segment 162*b* has a next-best ranking. Accordingly, the segment 162*a* may be part of a first-line treatment protocol and the segment 162*b* may be used if, for a particular subject, the segment 162*a* is not effective. Further, as disclosed herein, subsequent doses may be moved around the organ such that the subsequent doses are distributed to different segments (162*b*, 162*c*, 162*d*).

In certain cases, the user may wish to capture multiple organs at a single stimulation site. The region of interest 20 may be selected to encompass segments that overlap between the organs 150, 152. For example, the region of interest 20 may be within segment 160*h* of the first organ and segment 162*d* of the second organ 162.

In an embodiment, the system may distribute the ultrasound energy dose between multiple regions of interest 20. The distribution may be generally equal or may be skewed such that one or more regions of interest 20 receive more ultrasound energy that other regions. For example, if an ultrasound energy dose for a particular treatment is set at 400 m/W cm$^2$ to be distributed between two different regions of interest, a first region of interest 20 corresponding to the selected segment 160*a* and a second region of interest 20 corresponding to the selected segment 162*a*, the dose energy may be distributed at ratios of 1:1-1:2, 1:1-1:3, 1:1-1:5, or 1:1-1:10 between the two regions of interest 20. For example, 75-90% of a dose may be applied to one region of interest 20 while 10-25% of the dose is applied to another region of interest 20. When three regions of interest 20 are present, the dose may be distributed at ratios of 1:1:1-1:2:1, 1:1:1-1:2:2, 1:1:1-1:3:1, 1:1:1-1:3:3, 1:1:1-1:5:1, 1:1:1-1:5:5, 1:1:1-1:10:1, or 1:1:1-1:10:10 between the three regions of interest 20. The distribution ratio may be selected based on organ type and/or organ size. For example, particular organs may be associated with more responsiveness at lower dose distributions. Accordingly, a multi-site dose may be distributed with a greater percentage of the dose being applied to less responsive regions of interest 20 (or organs) while more responsive regions of interest 20 may require less energy to achieve desired effects. In this manner, the dose may be more efficiently applied to the patient and in a manner that minimizes overall ultrasound energy exposure. Further, because ultrasound energy may be focused on responsive regions of interest 20, off-target exposure may be minimized.

As provided herein, the effectiveness of the neuromodulation may be assessed, and the system may track effectiveness of ultrasound energy applied to different segments. The assessment may be via proxy markers, such as concentration changes in one or more molecules of interest that serve as indicators of tissue displacement as a result of ultrasound energy. In one embodiment, a certain segment may be associated with effective treatment for a general population of subjects. However, an individual subject may not achieve the desired effectiveness when ultrasound energy is applied to the region of interest 20 associated with the segment. A subsequent dose may be distributed to different segments to account for patient-to-patient variability in treatment responsiveness.

The disclosed techniques may also avoid physiological compensation effects for subsequent doses by tracking the location of the regions of interest 20 used for previous treatments and automatically distributing subsequent doses to regions of interest 20 associated with different segments. Further, the system may track overall energy applied to each segment over the course of a treatment protocol that may occur over days, weeks, or months, and may use rules-based logic to limit total energy applied to each individual segment below a predetermined threshold over a particular time window. Further, the system may also use the same segments for subsequent doses, but may change the dose distribution between segments for an individual dose. In one example, if the segment 160*b* receives more than 50% of a first dose while segments 160*b* and 162*a* each receive less than 25%, the same segment 160*b* may receive only 25% or less of a subsequent dose.

Figure 15:
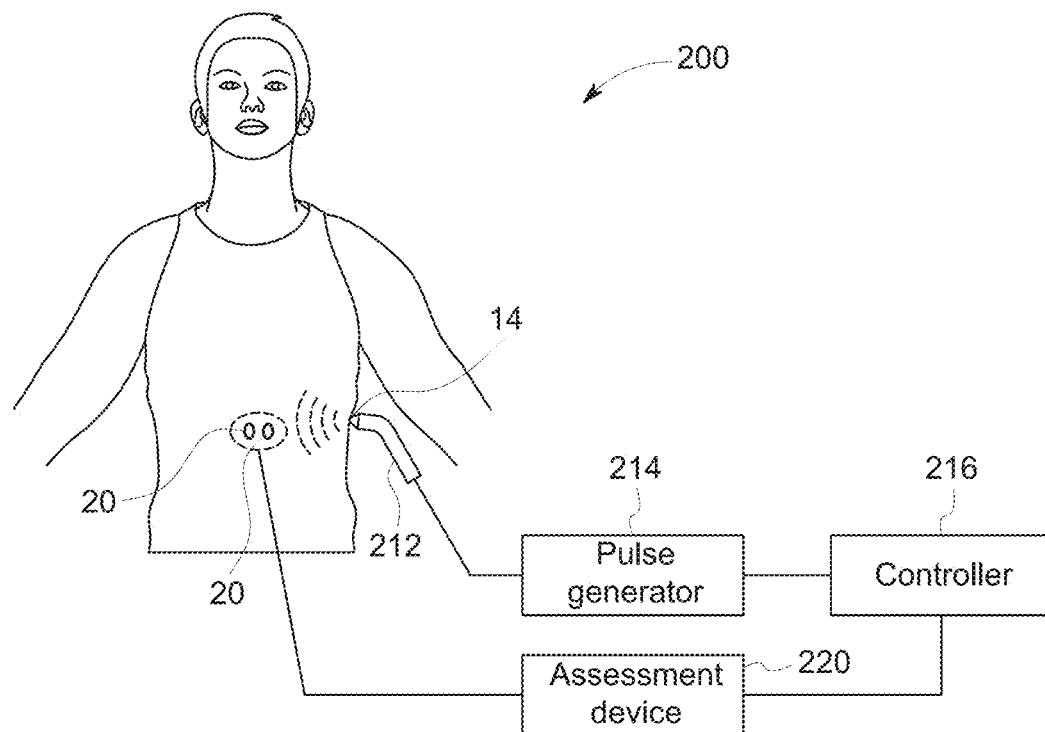
FIG. 15 is a schematic representation of an ultrasound neuromodulation system according to embodiments of the disclosure.

FIG. 15 shows a system 200 for neuromodulation to achieve neuromodulating effects such as tissue displacement at multiple regions of interest 20 associated with neurotransmitter release and/or activation of components (e.g., the presynaptic cell, the postsynaptic cell) of a synapse in response to an application of energy. The depicted system includes a pulse generator 214 coupled to an energy application device 212 (e.g., that includes the ultrasound transducer 14). The energy application device 212 is configured to receive energy pulses, e.g., via leads or wireless connection, that in use are directed to multiple regions of interest 20 in one or more internal tissues or organ/s of a subject, which in turn results in a targeted physiological outcome.

In certain embodiments, the energy application device 212 and/or the pulse generator 214 may communicate wirelessly, for example with a controller 216 that may in turn provide instructions to the pulse generator 214. In other embodiments, the energy application device 212 may be an extracorporeal device, e.g., may operate to apply energy transdermally or in a noninvasive manner from a position outside of a subject's body, and may, in certain embodiments, be integrated with the pulse generator 214 and/or the controller 216. In embodiments in which the energy application device 212 is extracorporeal, the energy application device 212 may be operated by a caregiver and positioned at a spot on or above a subject's skin such that the energy pulses are delivered transdermally to a desired internal tissue. Once positioned to apply energy pulses to the desired region of interest 20, the system 200 may initiate neuromodulation of one or more nerve pathways to achieve targeted physiological outcome or clinical effects. In other embodiments, the pulse generator 214 and/or the energy application device 212 may be implanted at a biocompatible site (e.g., the abdomen) and may be coupled internally, e.g., via one or more leads. In some embodiments, the system 200 may be implemented such that some or all of the elements may communicate in a wired or wireless manner with one another.

In certain embodiments, the system 200 may include an assessment device 220 that is coupled to the controller 216 and that assesses characteristics that are indicative of whether the targeted physiological outcome of the modulation have been achieved. In one embodiment, the targeted physiological outcome may be local. For example, the modulation of one or more nerve pathways may result in local tissue or function changes, such as tissue structure changes, local change of concentration of certain molecules, tissue displacement, increased fluid movement, etc. The targeted physiological outcome may be a goal of the treatment protocol.

The modulation of one or more nerve pathways to achieve a targeted physiological outcome may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 220 may be configured to assess concentration changes in some embodiments. In some embodiments, the assessment device 220 may be an imaging device configured to assess changes in organ size position, and/or tissue characteristics. In another embodiment, the assessment device 220 may be a circulating glucose monitor. While the depicted elements of the system 200 are shown separately, it should be understood that some or all of the elements may be combined with one another. In another embodiment, the assessment device may assess local temperature rises of the tissue, which may be detected using a separate temperature sensor or ultrasound imaging data from the energy application device 212 when configured for ultrasound energy application. Assessment of speed of sound differences may be detected through difference imaging techniques pre/during/post therapy.

Based on the assessment, the modulation parameters of the controller 216 may be altered such that an effective amount of energy is delivered. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 216, either by an operator or via an automatic feedback loop, for defining or adjusting the energy application parameters or modulation parameters of the pulse generator 214 until the modulation parameters result in an effective amount of energy being applied. In one embodiment, an initially defined region of interest may be refined to yield an updated region of interest based on feedback from the assessment device as to the efficacy of the neuromodulating energy over the course of the treatment protocol. The feedback may be, for example, changes in concentration of molecules of interest as a result of the application of neuromodulating energy. These refinements or updates to the region of interest may be used as part of patient-specific networks, where the network is updated to identify the specific region of interest that has the most impact on the physiological parameters of interest for that particular individual based on the desired clinical outcome.

The system 200 as provided herein may provide energy pulses according to various modulation parameters as part of a treatment protocol to apply the effective amount of energy. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. Further, the treatment protocol may specify a time of day to apply energy or a time relative to eating or other activity. The treatment duration to cause the targeted physiological outcomes may last for various time periods, including, but not limited to, from a few minutes to several hours. In certain embodiments, treatment duration with a specified stimulation pattern may last for one hour, repeated at, e.g., 72 hour intervals. In certain embodiments, energy may be delivered at a higher frequency, say every three hours, for shorter durations, for example, 30 minutes. The application of energy, in accordance with modulation parameters, such as the treatment duration, frequency, and amplitude, may be adjustably controlled to achieve a desired result.

Figure 16:
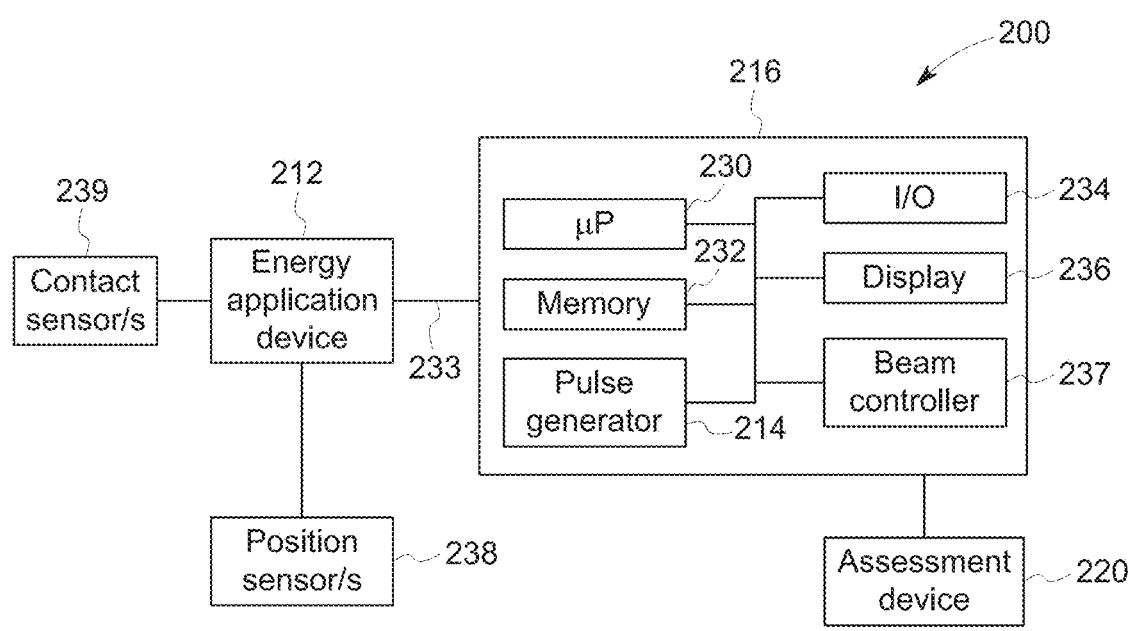
FIG. 16 is a block diagram of an ultrasound neuromodulation system according to embodiments of the disclosure.

FIG. 16 is a block diagram of certain components of the system 200. As provided herein, the system 200 for neuromodulation may include a pulse generator 214 that is adapted to generate a plurality of energy pulses for application to a tissue of a subject. The pulse generator 214 may be separate or may be integrated into an external device, such as a controller 216. The controller 216 includes a processor 230 for controlling the device. Software code or instructions are stored in memory 232 of the controller 216 for execution by the processor 230 to control the various components of the device. The controller 216 and/or the pulse generator 214 may be connected to the energy application device 212 via one or more leads 233 or wirelessly.

The controller 216 may include a user interface with input/output circuitry 234 and a display 236 that are adapted to allow a clinician to provide selection inputs (e.g., selecting a region of interest 20 or a particular segment on an image of the target tissue that is associated with a desired region of interest 20) or modulation parameters to modulation programs. The processor 230 may be configured to operate to identify one or more organs or tissue structures within image data and to divide the organs or tissue structures into segments. Further, the processor 230 may be configured to apply ultrasound energy to the subject at one or more regions of interest associated with particular segments.

The system may include a beam controller 237 that may control a focus location of the energy beam of the transducer 14 of the energy application device 212 by controlling one or both of steering and/or focusing of the energy application device 212 to apply concurrent multi-beam treatment or consecutive beam treatment to one or more tissues. The beam controller 237 may also control or one or more articulating portions of the energy application device 212 to reposition the transducer. The beam controller may receive instructions from the processor 230 to cause changes in focusing and/or steering of the energy beam. The system 200 may be responsive to position sensor/s 238 and/or contact sensor/s 239 that provide feedback on the energy application device 212. The beam controller 237 may include a motor to facilitate steering of one or more articulating portions of the energy application device 212. It is contemplated that the system 200 may include features to permit position, steering, and/or focus adjustments to facilitate the techniques disclosed herein.

Each modulation program stored in the memory 232 may include one or more sets of modulation parameters including pulse amplitude, pulse duration, pulse frequency, pulse repetition rate, etc. The pulse generator 214 modifies its internal parameters in response to the control signals from controller device 216 to vary the stimulation characteristics of energy pulses transmitted through lead 233 to a subject to whom the energy application device 212 is applied. Any suitable type of pulse generating circuitry may be employed, including but not limited to, constant current, constant voltage, multiple-independent current or voltage sources, etc. The energy applied is a function of the current amplitude and pulse duration. The controller 216 permits adjustably controlling the energy by changing the modulation parameters and/or initiating energy application at certain times or suppressing energy application at certain times. In one embodiment, the adjustable control of the energy application device to apply energy is based on information about a concentration of one or more molecules in the subject (e.g., a circulating molecule).

If the information is from the assessment device 220, a feedback loop may drive the adjustable control. For example, a diagnosis may be made based on circulating glucose concentration, as measured by the assessment device 220, in response to neuromodulation. When the concentration is above a predetermined threshold or range, the controller 216 may initiate a treatment protocol of energy application to a region of interest (e.g., spleen) and with modulation parameters that are associated with a reduction in circulating glucose. The treatment protocol may use different modulation parameters than those used in the diagnosis protocol (e.g., higher energy levels, more frequent application).

In one embodiment, the memory 232 stores different operating modes that are selectable by the operator. For example, the stored operating modes may include separate algorithms for identifying a particular region of interest and executing a set of modulation parameters associated with a particular treatment site, such as regions of interest in the liver, pancreas, gastrointestinal tract, spleen. Each organ or site may be associated with a different model. Further, different sites may have different associated modulation parameters based on the depth of the relevant organ, the size of the region of interest, the desired physiological outcome, etc. Rather than having the operator manually input the modes, the controller 216 may be configured to execute the appropriate instruction based on the selection of a particular organ. In another embodiment, the memory 232 stores operating modes for different types of procedures. For example, activation may be associated with a different stimulating pressure or frequency range relative to those associated with depressing or blocking tissue function.

In a specific example, when the energy application device is an ultrasound transducer, the effective amount of energy may involve predetermined temporal average intensity applied to a region of interest. For example, the effective amount of energy may include a time-averaged power (temporal average intensity) and peak positive pressure in the range of 1 mW/cm$^2$-30,000 mW/cm$^2$ (temporal average intensity) and 0.1 MPa to 7 MPa (peak pressure). In one example, the temporal average intensity is less than 35 mW/cm$^2$, less than 500 mW/cm$^2$, or less than 720 mW/cm$^2$ in the region of interest. In an example, the temporal average intensity is associated with levels less than those associated with thermal damage and ablation/cavitation. The controller 216 may be capable of operating in a validating mode to acquire a predetermined treatment position and the predetermined treatment position may be implemented as part of a treatment operating mode that is configured to execute a treatment protocol when the energy application device 212 is positioned at the predetermined treatment position.

The system may also include an imaging device that facilitates focusing the energy application device 212. In one embodiment, the imaging device may be integrated with or the same device as the energy application device 212 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 232 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 212 may be focused (e.g., using the beam controller 237) to a focus location on the selected volume corresponding to the region of interest. It should be understood that the image data used to guide the focus location may be a volume or a plane. For example, the energy application device 212 may be configured to first operate in the validating mode to acquire the predetermined treatment position by capturing image data to be used for identifying the predetermined treatment position associated with capturing the region of interest. The validating mode energy is not at levels and/or applied with modulation parameters suitable for neuromodulating treatment. However, once the region of interest is identified, the controller 216 may then operate in a treatment mode according to the modulation parameters associated with achieving targeted physiological outcomes.

The target tissue may be an internal tissue or an organ that includes synapses of axon terminals and non-neuronal cells. The synapses may be stimulated by direct application of ultrasound energy to the axon terminals within a field of focus of the ultrasound transducer focused on a region of interest 20 of the target tissue to cause release of molecules into the synaptic space. The region of interest may be selected to include a certain type of axon terminal, such as an axon terminal of a particular neuron type and/or one that forms a synapse with a certain type of non-neuronal cell. Accordingly, the region of interest 20 may be selected to correspond to a portion of the target tissue with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction, or cause an activation within both the neural and non-neuronal cells that elicits a desired physiological effect.

The controller 216 may also be configured to receive inputs related to the targeted physiological outcomes as an input to the selection of the modulation parameters. For example, when an imaging modality is used to assess a tissue characteristic, the controller 216 may be configured to receive a calculated index or parameter of the characteristic. Based on whether the index or parameter is above or below a predefined threshold, a diagnosis may be made, and an indication of the diagnosis may be provided (e.g., via a display). In one embodiment, the parameter may be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 212 (e.g., an ultrasound transducer) may operate under control of the controller 216 to a) acquire image data of a tissue that may be used to spatially select a region of interest within the target tissue b) apply the modulating energy to the region of interest and c) acquire image data to determine that the targeted physiological outcome has occurred (e.g., via displacement measurement). In such an embodiment, the imaging device, the assessment device 220 and the energy application device 212 may be the same device.

Technical effects of the present disclosure include controlled application of multi-site neuromodulating energy (e.g., ultrasound energy) that avoids physiological compensation effects and that adjusts dosage based on the selected region of interest (e.g., stimulation site) such that overall energy applied to the patient is minimized. In this manner, neuromodulation systems may expend less energy and may operate more efficiently. Multiple stimulation sites for a single energy dose may be selected such that the physiological effects of the neuromodulating energy augment one another. In one example, stimulation of the spleen resulted in a reduction in glucose, while stimulation of the pancreas and spleen together resulted in greater glucose reduction effects, due to concurrent insulin release from the pancreas. Further, the insulin release also resulted in a concurrent immune state change of the patient, which may be associated with desired physiological outcomes. However, the disclosed experimental results are by way of example, and the technical effects of the present disclosure may be applied to other multi-site stimulation cases.

This written description uses examples, including the best mode, and also to enable any person skilled in the art to practice the disclosed techniques, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound system, comprising:
   an ultrasound transducer comprising a plurality of individually addressable elements configured to distribute a dose of ultrasound energy between a plurality of regions of interest in a subject; and
   a controller configured to:
      control the dose applied by the plurality of individually addressable elements between the plurality of regions of interest;
      receive ultrasound image data of tissue of the subject from the ultrasound transducer while the ultrasound transducer is operating in an imaging mode;
      divide the ultrasound image data of the tissue into a plurality of segments representative of the tissue;
      receive input on selection of a single region of interest;
      selecting a plurality of regions of interest based on the selected single region of interest, each region of interest of the plurality of regions of interest being located within a different segment of the plurality of segments, wherein a first segment of the plurality of segments is nonadjacent to a second segment of the plurality of segments;
      focus the ultrasound transducer on the selected plurality of regions of interest;
      control the ultrasound transducer in a treatment mode to distribute the dose of ultrasound energy between the plurality of regions of interest to neuromodulate two or more neural pathways of the subject, wherein the ultrasound energy is associated with levels less than those associated with ablation of the tissue, and wherein the neuromodulation of the two or more neural pathways induces a physiological effect; and
      receive input related to the induced physiological effect.

2. The system of claim 1, wherein the tissue comprises a first organ and a second organ different than the first organ, and wherein a first region of interest of the plurality of regions of interest is in the first organ and a second region of interest of the plurality of regions of interest is in the second organ.

3. The system of claim 2, wherein 75%-90% of the dose is applied to the first organ.

4. The system of claim 2, wherein the first organ is a pancreas, spleen, or liver.

5. The system of claim 1, wherein the tissue comprises an organ, and wherein the plurality of regions of interest are in the organ.

6. The system of claim 1, wherein the controller is configured to control applying the dose such that no individual segment of the plurality of segments receives more than a selected threshold of ultrasound energy over a time period and wherein the dose is applied to multiple segments of the plurality of segments.

7. The system of claim 1, wherein the controller is configured to apply the ultrasound energy concurrently to each region of interest.

8. The system of claim 1, wherein the controller is configured to apply the ultrasound energy in series to each region of interest.

9. The system of claim 1, wherein the controller is configured to control a first subset of the plurality of elements to apply a first ultrasound energy to a first region of interest of the plurality of regions of interest and a second subset of the plurality of ultrasound elements to apply a second ultrasound energy to a second region of interest of the plurality of regions of interest.

10. The system of claim 9 wherein the first region of interest is in a first organ and the second region of interest is in a second organ different than the first organ, and wherein the first ultrasound energy is a greater fraction of the dose than the second ultrasound energy.

11. The system of claim 1, wherein the controller is configured to use updated ultrasound image data and the ultrasound image data to measure tissue displacement and modify parameters of the dose based on the measured tissue displacement.

12. The system of claim 11, wherein the controller modifies the parameters by changing a relative distribution of ultrasound energy between the plurality of regions of interest for a subsequent ultrasound energy application.

13. An ultrasound system, comprising:
   an ultrasound transducer comprising a plurality of elements; and
   a controller comprising a memory, wherein the memory stores instructions to control a dose of ultrasound energy applied to a subject by the ultrasound transducer that, when executed by the controller, cause the controller to:
      receive image data of tissue of the subject from the ultrasound transducer;
      divide the image data of the tissue into a plurality of segments representative of the tissue;
      receive input selecting a single region of interest;

focus the ultrasound transducer on a plurality of regions of interest based on the selected single region of interest, each region of interest being located within a different segment of the plurality of segments;

control the ultrasound transducer to apply ultrasound energy distributed between the plurality of regions of interest, wherein the plurality of regions of interest are spaced apart from the selected region of interest;

monitor a concentration change relative to baseline of one or more molecules; and modify the instructions based on the concentration change.

14. The system of claim 1, wherein the controller is configured to apply the ultrasound energy to a first segment comprising a first selected region of interest and to a second segment comprising a second selected region of interest.

15. The system of claim 13, wherein a first segment is nonadjacent to the second segment.

16. The system of claim 1, wherein the input related to the induced physiological effect comprises a value of a measured parameter, and wherein controller is configured to determine that the value corresponds to an expected value of the measured parameter.

17. The system of claim 1, wherein the input related to the induced physiological effect comprises a value of a measured parameter, and wherein controller is configured to:

determine that the value does not correspond to an expected value of the measured parameter; and automatically select a different region of interest based on the determining.

18. The system of claim 1, wherein the input related to the induced physiological effect comprises a value of a measured parameter, and wherein controller is configured to:

determine that the value deviates from an expected value of the measured parameter, wherein the expected value is associated with ultrasound energy application to the single region of interest.

19. The system of claim 18, wherein the controller is configured to:

modify a modulation parameter of the treatment mode-based on the deviation and controlling the ultrasound using the modified parameter.

* * * * *